United States Patent [19]

Gerber

[11] 4,030,198
[45] June 21, 1977

[54] TOOTH ENAMEL-STRIPPING APPARATUS
[75] Inventor: Warren E. Gerber, LaJolla, Calif.
[73] Assignee: Evalyn Gerber, LaJolla, Calif.
[22] Filed: Sept. 30, 1974
[21] Appl. No.: 510,320
[52] U.S. Cl. .................................................. 32/58
[51] Int. Cl.² ............................................ A61C 3/06
[58] Field of Search ............. 32/40 R, 46, 58, 382; 132/91, 92, 75.6, 76.4, 76.5; 51/386, 392, 380; 145/33 C, 33 A

[56] References Cited

UNITED STATES PATENTS

| | | | |
|---|---|---|---|
| 1,050,469 | 1/1913 | Keifer | 32/46 |
| 1,201,875 | 10/1916 | Russ | 32/58 |
| 1,913,598 | 6/1933 | Keefe | 32/46 X |
| 1,970,575 | 8/1934 | Reitzel | 132/91 |
| 2,176,069 | 10/1939 | Goulet | 132/91 |
| 2,207,953 | 7/1940 | Summerbell | 132/91 |
| 2,337,388 | 12/1943 | Hawkins | 132/75.6 |
| 2,500,867 | 3/1950 | Reiter | 32/63 |
| 2,648,341 | 8/1953 | Moll | 132/91 |
| 2,664,093 | 12/1953 | Carpenter | 132/91 |

FOREIGN PATENTS OR APPLICATIONS 644,176   5/1928   France .................................. 132/91

*Primary Examiner*—Robert Peshock
*Attorney, Agent, or Firm*—Merriam, Marshall, Shapiro & Klose

[57] ABSTRACT

A hand-held, tooth enamel-stripping apparatus having a handle portion, and a guiding portion extending from the handle portion to a free end. One end of an abrasive metal band is secured to a U-shaped member connected to the free end of the guiding portion, and the other end of the band is tensionably secured to a locking mechanism, spaced from the U-shaped member, and connected to the handle portion. The band is mounted to the apparatus adjacent the guiding portion so that when the band is inserted between adjacent teeth, the guiding portion rests adjacent a tooth crown for guiding the apparatus during its reciprocal, tooth-stripping movement.

2 Claims, 6 Drawing Figures

U.S. Patent   June 21, 1977   4,030,198
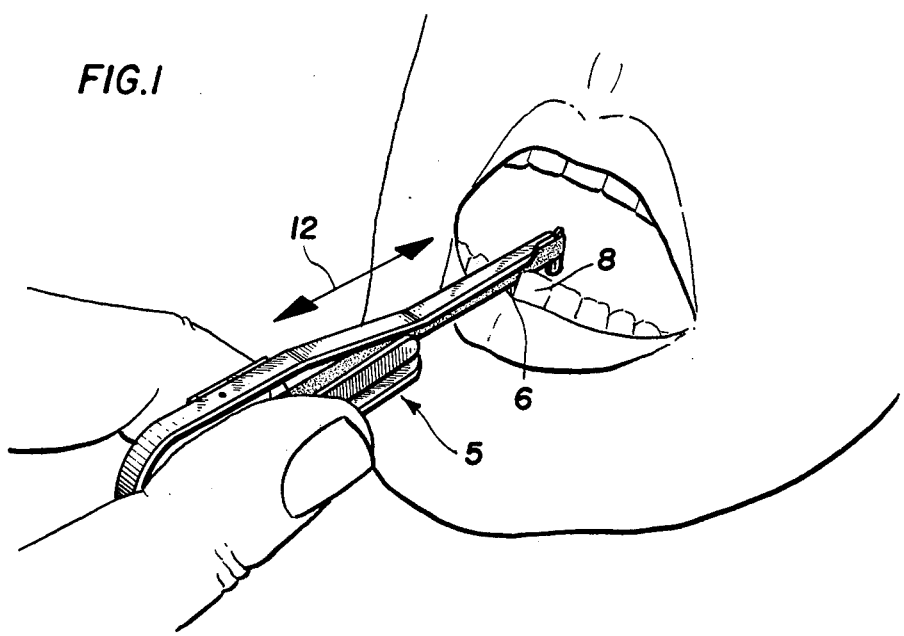
FIG.1
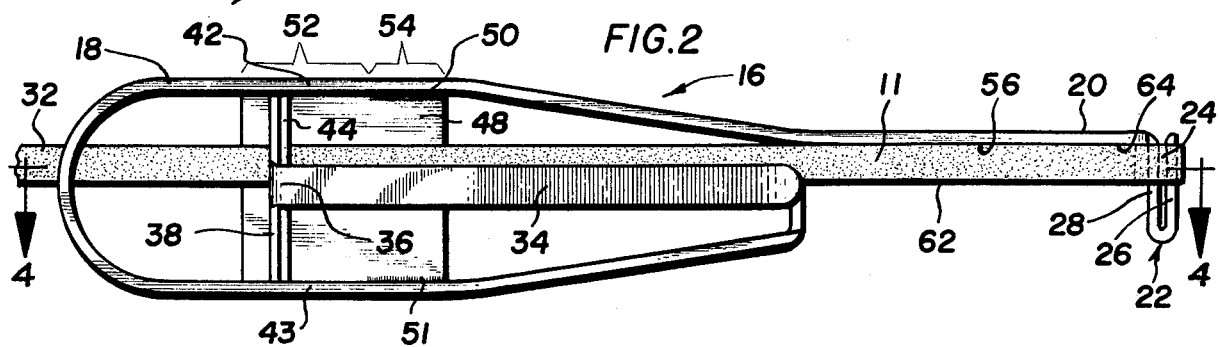
FIG.2
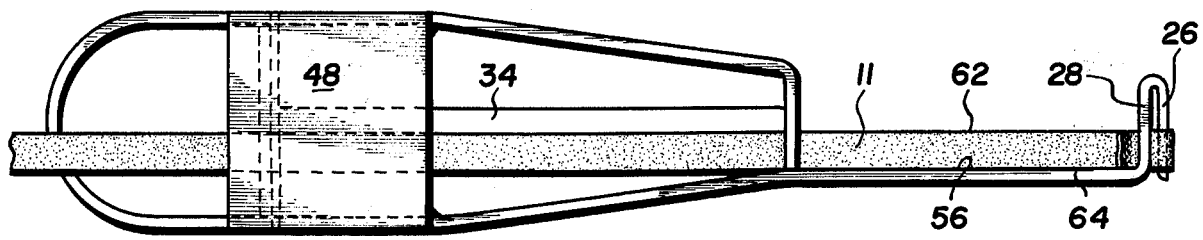
FIG.3
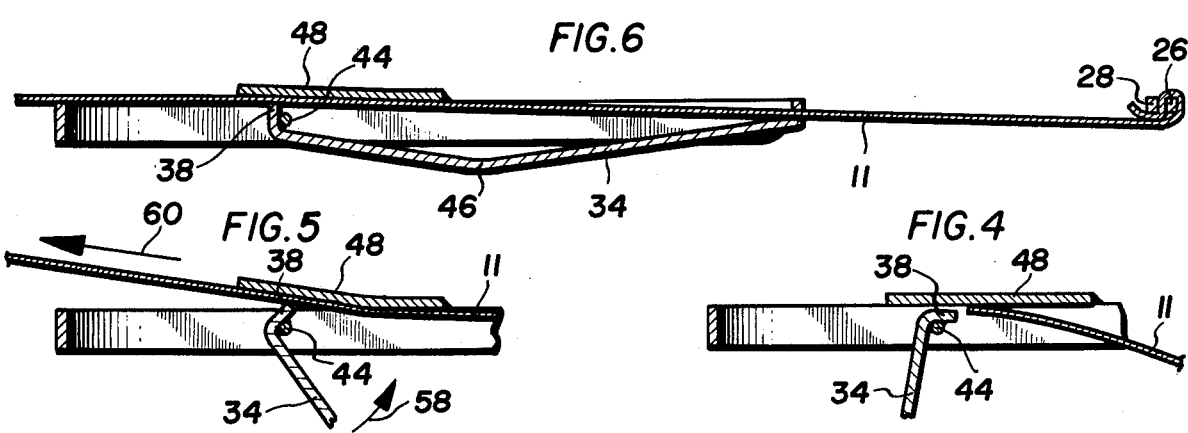
FIG.6
FIG.5
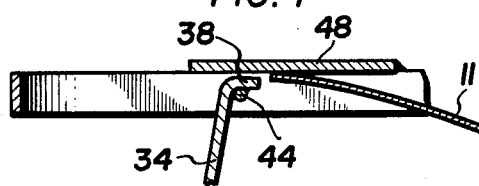
FIG.4

TOOTH ENAMEL-STRIPPING APPARATUS

BACKGROUND OF THE INVENTION

1. Field of Invention

The present invention pertains generally to dental instruments and more particularly, to a hand-held orthodontic apparatus which tensionably secures an abrasive metal band for stripping dental enamel.

2. Description of the Prior Art

In the field of dentistry it is often necessary to strip dental enamel off tooth surfaces. This procedure is employed generally for the purpose of aiding in the elimination of teeth crowding, modifying irregular tooth surfaces or creating space between teeth for proper orthodontic band or crown fitting and cementation.

It is common practice to strip dental enamel by inserting a segment of an abrasive metal band adjacent a patient's tooth and to manually pull each band end in a reciprocal motion until the desired amount of enamel is filed away. Enamel stripping or reduction is hard to control when using this technique, because it is physically difficult to hold and manipulate the band, under the required amount of tension, within the small confines of the mouth. Handling difficulty is further caused by the fact that it is common for the dentist to cut his fingers when manipulating the sharp metal band. Indeed, it is also common for the patient to experience unusual discomfort during this procedure as well as injury, since a slight slip of the hand can cause the metal band to lacerate the patient's gum tissues.

The prior art includes an apparatus which essentially consists of an abrasive band that is permanently mounted within a plastic frame. The entire apparatus is disposed of after the abrasive quality of the band has been depleted. One type of such apparatus rigidly encases a segment of an abrasive band along the band's top and end edges. Another type of apparatus flexibly encases an abrasive band only along the band's end edges. Since a rigid band is not as effective as a flexible band for shaping irregular tooth surfaces, it becomes necessary to alternately use both the rigidly encased band and the flexibly encased band when tight tooth contacts and irregular tooth surfaces are to be reduced. Thus, use of this prior art wastes band material since a single band usually has enough abrasion for most multiple reduction procedures. In addition, this prior art has no means for varying the tension on the abrasive band.

What is desired, therefore, is an apparatus which is capable of securing a single abrasive band under varying degress of tension to facilitate the accurate as well as safe reduction of tight tooth contacts as well as irregular tooth surfaces.

BRIEF SUMMARY OF THE INVENTION

The present invention relates to a hand-held apparatus for stripping tooth enamel and which is capable of holding variously sized abrasive metal bands under varying degress of tension.

The present invention utilizes a frame including a guiding portion and U-shaped securing means on the guiding portion for releasably securing a first end of an abrasive band. The present invention further utilizes locking means on the frame and spaced from the guiding portion, for tensionably securing a second end of the abrasive band.

The unique locking arrangement of the present invention permits a band segment, taken from standard stock, to be secured to the frame under varying degrees of tension. Thus, the band segment may be rigidly secured to the apparatus of the present invention when it is required, for example, to reduce tight tooth contacts. Alternatively, the same band may be flexibly secured to the apparatus of the present invention if it is desired, for example, to shape irregular tooth surfaces. Thus, the apparatus of the present invention permits a single abrasive band to be interchangeably, and thus economically, used for multiple reduction procedures.

The present invention is capable of accommodating the mounting of variously sized bands adjacent the guiding portion so that the band may be inserted between adjacent teeth until the guiding portion rests adjacent a tooth crown for guiding the apparatus during use. This arrangement also helps to reduce the incidence of gum tissue injury since the guiding portion acts as a "backstop" to prevent the band edge from contacting the vulnerable gum tissues when the width of the band is less than the length of the exposed tooth surface.

The apparatus may also be used as an aid in reducing filling material on tooth surfaces and as an aid in placing fillings where tooth contacts are tight.

Other features and advantages of the present invention will become apparent to those skilled in the art from the following detailed description in conjunction with the accompanying drawing.

BRIEF DESCRIPTION OF THE DRAWING

FIG. 1 is a perspective of an embodiment of the invention in use in a human mouth;

FIG. 2 is a front view of the embodiment of FIG. 1 with the lever arm thereof in a closed position;

FIG. 3 is a rear view of the embodiment of FIG. 1;

FIG. 4 is a partial sectional view essentially along line 4—4 of FIG. 2 but with the lever arm in a first or open position;

FIG. 5 is a partial sectional view like FIG. 4 but showing the lever arm in a second or tensioning position; and, FIG. 6 is a sectional view like FIG. 4 but showing the lever arm in a third or closed position, as in FIG. 2.

DETAILED DESCRIPTION

Referring initially to FIG. 1, the apparatus of the present invention is designated generally at 5. A segment of abrasive metal band 11 is attached to apparatus 5 and has a distal portion inserted, for example, between teeth 6, 8 for reciprocal movement generally in the direction of double arrow 12 to create a space between the teeth.

Apparatus 5 comprises a frame 16 formed out of a strip of stainless steel and includes a handle portion 18 and a guiding portion 20, extending longitudinally from and coplanar with handle portion 18.

It is desired that handle portion 18 be of a length and width to permit the apparatus to be held comfortably between a user's fingers (see FIG. 1).

U-shaped securing means 22, connected to guiding portion 20, releasably secures a first end 24 of the abrasive metal band 11 to frame 16. U-shaped member 22 comprises a hook portion 26 narrowly spaced from a shank portion 28 at a distance no greater than the thickness of band 11 to insure that band 11 may be securely wound around hook 26 and shank 28 (see FIG. 6).

A locking mechanism is operatively mounted to the handle portion 18 for releasably securing a second end 32 of band 11 to frame 16 and for regulating the tension of band 11. The locking mechanism comprises a lever arm 34, having an end 36 connected to a base portion 38 extending between sides 42, 43 respectively, of handle portion 18, and mounted on a pivot pin 44 for rotation with lever arm 34 about the pivotal axis of pin 44. Lever arm 34 is bent at 46 to facilitate the grasping of the lever arm (see FIG. 6). Base portion 38 may be mounted on pin 44 by soldering or welding.

To complete the locking mechanism, lever biasing means, such as a leaf spring 48 is mounted to sides 42, 43 of handle portion 18 by soldering at 50, 51 respectively (see FIG. 2). By mounting leaf spring 48 to handle portion 18 in this manner, leaf spring 48 is thereby divided into two portions, one portion 52 being free and the other portion 54 being firmly secured to handle portion 18 (see FIG. 2). Leaf spring 48 should be mounted to handle portion 18 so that free portion 52 is adjacent base portion 38 to permit lever arm 34 to tensionably secure second band end 32 when leaf spring 48 and base portion 38 are in biasing engagement (see FIG. 5).

Abrasive band 11 is easily attached to apparatus 5 be securing first band end 24 to U-shaped member 22. This is accomplished by threading first band end 24 around shank 28 and hook 26 (see FIG. 6). With lever arm 34 in a first or open position (FIG. 4) base position 38 does not contact leaf spring 48 and second band end 32 may then be inserted and positioned between base portion 38 and leaf spring 48 and positioned so that band edge 56 lies adjacent guiding portion surface 64 (FIG. 2 and 3). Second band end 32 may be then pulled with the fingers of one hand to make band 11 as taut as desired. Lever arm 34 is then rotated in the directed of arrow 58 to a second or tensioning position wherein base portion 38 is in contact with leaf spring 48 (see FIG. 5). The biasing force of leaf spring 48 against base portion 38 causes band 11 to be pulled in the direction of arrow 60 and further tightened. Lastly, lever arm 34 is rotated to a third or closed position wherein base portion 28 still remains in contact with leaf spring 48 to securely lock band 11 to frame 16 (see FIG. 6).

Since the apparatus of the present invention is capable of tensionably locking abrasive bands of various widths, it is advantageous to use a band having a width no wider than the exposed tooth surface (i.e., the distance from the tooth crown to the gum tissues). By mounting a band having the desired width adjacent guiding portion 20, band edge 62 should not contact the gum tissues during normal use, because as guiding portion 20 moves adjacent the tooth crown, the distance from band edge 62 to guiding portion surface 64 is less than the length of the exposed tooth surface. Thus, guiding portion 20 effectively acts as a "backstop "to help prevent band edge 62 from contacting, and thus lacerating, vulnerable gum tissues.

Band 11 should be rigidly secured to frame 16 when tooth contacts are tight, because it is difficult to insert a flexible band between tight tooth contacts. However, when tooth contacts are extremely tight and the abrasive band cannot be passed therebetween, it may be necessary to first use a separating material, such as a wire or piece of thin plastic, to facilitate insertion of the band. As previously noted, band 11 may also be flexibly secured to frame 16 when it is desired, for example, to shape irregular tooth surfaces. Thus, a single band may be used for multiple reduction procedures.

It is to be noted that during use, the abrasive band may be washed occasionally in water to prevent clogging and to improve filing. After reduction, the worn abrasive band may be used for polishing the tooth enamel.

The apparatus should be made out of suitable corrosion resistant material, and it is preferred that the apparatus be formed, for example, out of a strip of stainless steel approximately 3/16 inch wide and 0.031 inch thick.

Use of the apparatus of the present invention is not intended to be limited to enamel reduction procedures since the apparatus may also be effectively used be machinists or model makers and the like for fine filing or deburring.

It will further be understood that the embodiments described herein represent the preferred embodiments of the invention and that the invention is not intended to be limited to the particular details so illustrated and described, but encompasses all embodiments falling within the scope of the appended claims.

What is claimed is:

1. an orthodontic apparatus, for use with an abrasive band having a first end and a second end, to strip enamel from a tooth have a crown, said apparatus comprising:

a frame including a guiding portion;
means on said guiding portion for releasably securing said first end of said abrasive band;
lever means including a base portion;
biasing means on said frame spaced from said guiding portion for engagement with said lever means; and,
means mounting said lever means adjacent said biasing means for movement of said lever means between:

a. a first position wherein said base portion is not in contact with said biasing means to permit said second band end to be inserted between said base portion and said biasing means;
b. a second position wherein said base portion is in contact with said second band end and said biasing means for tensioning said abrasive band; and,
c. a third position wherein said base portion is in contact with said second band end and said biasing means for locking said abrasive band.

2. An apparatus as set forth in claim 1 wherein said biasing means comprises:

a leaf spring including a free end; and,
means mounting said leaf spring to said frame for movement of said free end in response to the movement of said lever means.

* * * * *

UNITED STATES PATENT AND TRADEMARK OFFICE
CERTIFICATE OF CORRECTION

PATENT NO. : 4,030,198

DATED : June 21, 1977

INVENTOR(S) : Warren E. Gerber

It is certified that error appears in the above-identified patent and that said Letters Patent are hereby corrected as shown below:

Column 3, line 27, change "be" to --by--;

line 38, change "directed" to --direction--.

stripping position--;

Column 4, line 22, change "be" to --by--;

Signed and Sealed this

Eleventh Day of October 1977

[SEAL]

Attest:

RUTH C. MASON
Attesting Officer

LUTRELLE F. PARKER
Acting Commissioner of Patents and Trademarks